United States Patent
Norrby

[11] Patent Number: 5,968,095
[45] Date of Patent: Oct. 19, 1999

[54] METHOD OF SELECTING AN INTRAOCULAR LENS TO BE IMPLANTED INTO AN EYE

[75] Inventor: Sverker Norrby, Landauerlaan, Netherlands

[73] Assignee: Pharmacia & Upjohn Groningen BV, Groningen, Netherlands

[21] Appl. No.: 08/945,036

[22] PCT Filed: May 3, 1996

[86] PCT No.: PCT/SE96/00577

§ 371 Date: Dec. 29, 1997

§ 102(e) Date: Dec. 29, 1997

[87] PCT Pub. No.: WO96/35396

PCT Pub. Date: Nov. 14, 1996

[30] Foreign Application Priority Data

May 9, 1995 [SE] Sweden .................................. 9501714

[51] Int. Cl.$^6$ ...................................................... A61F 2/16
[52] U.S. Cl. ................................................. 623/6; 128/898
[58] Field of Search .................................. 623/6; 128/898

[56] References Cited

U.S. PATENT DOCUMENTS 4,710,193 12/1987 Volk ............................................ 623/6
5,282,852 2/1994 Capetan et al. ............................. 623/6

OTHER PUBLICATIONS

Norrby, *Eur. J. Implant. Ref. Surg*, 7, pp. 202–209 (Aug. 1995).
Norrby et al, *J. Cataract Refract. Surg*, 23, pp. 254–259(Mar. 1997).

*Primary Examiner*—Mickey Yu
*Assistant Examiner*—Kelly O'Hara
*Attorney, Agent, or Firm*—Dinsmore & Shohl LLP

[57] ABSTRACT

A method of preoperatively selecting an intraocular lens to be implanted into an eye to postoperatively render the eye emmetropic or ametropic with a desired postoperative refraction comprises determining the location of the lens haptic plane of the eye, the corneal power of the eye and the axial length of the eye, choosing the desired postoperative refraction and assuming a lens to be implanted, the lens having a known power and geometry, including an offset between the lens haptic plane and an anterior vertex of the lens as if it was in its implanted state. With these parameters and refractive indices of the ocular fluids, a calculation is made to determine whether or not, postoperatively, focus will fall on the retina of the eye. If, from the calculation, it is determined that focus will not fall on the retina of the eye, another lens with a different power and/or geometry is assumed to be implanted and the calculation is repeated until the focus is calculated to fall on the retina of the eye. A lens of the nearest power available for which focusing on the retina was calculated is then selected for implantation.

17 Claims, No Drawings

METHOD OF SELECTING AN INTRAOCULAR LENS TO BE IMPLANTED INTO AN EYE

TECHNICAL FIELD

The invention relates to a method of preoperatively selecting an intraocular lens to be implanted into an eye to postoperatively render the eye emmetropic or ametropic with any desired postoperative refraction.

BACKGROUND OF THE INVENTION

To obtain a desired postoperative refractive outcome of an intraocular lens implantation—emmetropia or ametropia—, there are several methods in use to determine which dioptric power the intraocular lens to be implanted, should have. The correct implant power to choose depends on the axial distance from the cornea, at which the intraocular lens (IOL) will end up in the eye.

With the present techniques, the axial position of the IOL can only be estimated.

Two major schools exist today for estimating the axial position of the IOL.

One school describes the optics of the eye in terms of thin lens theory.

In this connection reference is hereby made to:
1) Fedorov S N, Kolinko A L. Estimation of optical power of the intraocular lens. Vestn. Oftamol 1967;80(4):27–31,
2) Colenbrander M C. Calculation of the power of an iris clip lens for distant vision. Br J Ophthalmol 1973;57:735–740,
3) Hoffer K J. Mathematics and computers in intraocular lens calculation. Am Intra-Ocular Implant Soc J 1975;1 (1):4–5,
4) van der Heijde G L. A nomogram for calculating the power of the prepupillary lens in the aphakic eye. Bibliotheca Ophthalmol 1975;83:273–275,
5) Thijssen J M. The emmetropic and the iseikonic implant lens: computer calculation of the refractive power and its accuracy. Ophthalmologica 1975;171:467–486,
6) Binkhorst R D. The optical design of intraocular lens implants. Ophthalmic Surg 1975;6(3):17–31, and
7) Holladay J T, Prager T C, Chandler T Y, et al. A three-part system for refining intraocular lens power calculations. J Cataract Refract Surg 1988;14:17–24.

The axial position of the IOL is mostly considered to be a constant, often referred to as the ACD constant. The value of the constant depends to some extent on the IOL model. In the thin lens theory, this constant represents the postoperative distance between the principal planes of the cornea and of the IOL.

Another school applies retrospective statistical analysis of clinical data to determine a coefficient, the so called A-constant, in a linear equation, known as the SRK formula, linking corneal dioptric power K, eye length L, IOL power and postoperative refraction.

In this connection reference is made to:
8) Sanders D R, Retzlaff J, Kraff M, et al.: Comparison of the accuracy of the Binkhorst, Colenbrander, and SRK™ implant power prediction formulas. Am Intra-Ocular Implant Soc J 1981; 7:337–340,
9) Sanders D R, Retzlaff J, Kraff M C. Comparison of the SRKII™ formula and other second generation formulas. J. Cataract Refract Surg 1988;14:136–141, and
10) Sanders D R, Retzlaff J, Kraff M C, Gimbel H V, Raanan M G. Comparison of the SRK/T formula and other theoretical and regression formulas. J Cataract Refract Surg 1990; 16:341–346.

The linear relationship mentioned above, is not a theoretically correct representation of the optics of the eye, but the SRK approach is most widely used because it is simple and, in clinical practice, yields results similar to the thin lens theory approach.

The SRK/T formula in the above reference 10), is a hybrid between the two approaches.

In both schools, further refinement entails corrections depending on mainly eye length.

The following references:
11) Olsen T. Theoretical approach to intraocular lens calculation using Gaussian optics. J Cataract Refract Surg 1987; 13:141–145,
12) Haigis W. Strahldurchrechnung in Gausscher Optic zur Beschreibung des Linsen-Systems Brille-Kontaktlinse-Hornhaut-Augenlinse (IOL), in: Schott K, Jacobi K W, Freyler H (Hrsg): 4 Kongr. d. Deutsch. Ges. f. Intraokularlinsen Implant., Essen 1990. Berlin, Heidelberg, New York, Springer Verlag 1990, and
13) Kashiwagi T. Ray tracing error correction in ophthalmic optics. J Cataract Refract Surg 1991; 17:194–198,
apply thick lens theory, which is physically more exact, but the general problem of pre-estimating the axial position of the IOL remains.

The position of the IOL optic is determined by its fixation in the eye. Fixation is mostly obtained by means of attachments to the optic, so called loops, that hold the lens in place by spring action against ocular tissue. The most common site of placement of the IOL today is inside the capsular bag. Alternative placements are in the ciliary sulcus and in the anterior chamber angle. Lenses that are fixed to the iris also exist, but fixation is then not by spring action. There are also lenses meant for capsular bag placement that do not possess loops or exert spring action, such as disc lenses, plate lenses, and capsular bag filling lenses.

SUMMARY OF THE INVENTION

The object of the invention is to bring about a method of preoperatively selecting an intraocular lens to be implanted into an eye to postoperatively render the eye emmetropic or with any other chosen refractive outcome, which method should be applicable to all types of IOLs.

This is attained by the method according to the invention, which comprises the steps of
a) determining the location of the lens haptic plane of the eye,
b) determining the corneal power of the eye,
c) determining the axial length of the eye,
d) choosing the desired postoperative refraction,
e) assuming a lens to be implanted, said lens having a known power and geometry, including the offset between the haptic plane of said lens and the anterior vertex of said lens as if it was in its implanted state,
f) calculating from the parameters given by a), b), c), d) and e), as well as the refractive indices of ocular fluids, whether or not, postoperatively, focus will fall on the retina of the eye,
g) if that is not the case, repeating steps d)–f) assuming another lens with a different power and/or geometry, until focusing on the retina is calculated in step f), and
h) selecting for implantation, the lens of the nearest power available for which focusing on the retina is calculated in step f).

PREFERRED EMBODIMENTS

For all IOLs, a plane, the lens haptic plane (LHP), can be determined according to the invention. This plane is perpendicular to the optical axis of the eye and defines the plane of fixation of the IOL in the eye.

Given the location of this plane, i.e. actually its distance from the anterior cornea, the position of the optic in relation to it, is determined by the design of the lens.

For placement of the IOL in a particular site,.e.g. the capsular bag, this plane should be independent of the lens model. Given the corneal dioptric power K, or, which is equivalent, corneal thickness and radii, the eye length L, the location of the LHP from the anterior cornea, and the lens design, an exact calculation of the IOL dioptric power to render the eye emmetropic, or with any other desired refractive outcome, can be made according to the invention.

According to the invention, the following steps are carried out:

The location of the LHP of the eye in which the IOL is to be implanted is determined, as are, by methods known per se, the corneal power and the axial length of that eye. Moreover, the desired refractive outcome, usually emmetropia, is chosen.

Then, a lens having a known dioptric power and geometry as provided by the manufacturer, is assumed to be implanted.

Any offset between said determined LHP and the anterior vertex of the lens assumed to be implanted, is determined from the geometry of the lens, whereupon from the determined corneal power, the determined axial length, and the determined offset as well as the power and geometry of the assumed lens, and the refractive indices of cornea and ocular fluids, it is calculated whether-or not, postoperatively, the eye will obtain the desired refractive outcome with the assumed lens.

If that is not the case, another lens with a different power and/or geometry, is assumed, and the above calculations are repeated until focus on the retina is calculated. The lens of the nearest available power for which this is calculated, is then selected for implantation.

According to the invention, there are both indirect and direct methods available to preoperatively determine the location of the LHP, i.e. the distance from the anterior cornea to the LHP.

The distance from the anterior cornea to the anterior cataract can be measured by A-scan biometry. As mentioned above, this distance is termed ACD (ultrasonic or geometrical ACD). The thickness, LEN, of the cataract can also be determined by A-scan biometry. The distance from the anterior cornea to the LHP must be greater than ACD, since the IOL is placed within the subsequently empty capsular bag. The following formula is postulated:

$$LHP = ACD + \alpha \times LEN,$$

where $\alpha$ is a constant, which as suggested by preliminary analysis of clinical data, is between 0 and 0.25, preferably between 0.15 and 0.2. This method is somewhat indirect, but can be applied by means already in routine use.

Based on the same parameters, the following formula can also be used:

$$LHP = \beta \times (ACD + LEN),$$

where $\beta$ is a constant, which as suggested by preliminary analysis of clinical data, is between 0.3 and 0.7, preferably around 0.5.

With reference to:
14) Pavlin C J, Sherar M D, Foster F S. Subsurface ultrasonic microscopic imaging of the intact eye, Ophthalmology 1990; 97:244–250,
15) Pavlin C J, Harasiewicz K, Sherar M D, Foster F S. Clinical use of ultrasound biomicroscopy. Ophthalmology 1991; 98: 287–295,
16) Pavlin C J, Rootman D, Arshinoff S, et al. Determination of haptic position of transsclerally fixated posterior chamber intraocular lenses by ultrasound biomicroscopy. J. Cataract Refract Surg 1993; 19:573–577, and
17) Pavlin C J, Harasiewicz K, Foster F S. Ultrasound biomicroscopic analysis of haptic position in late-onset, recurrent hyphema after posterior chamber lens implantation. J Cataract Refract Surg 1994; 20:182–185, the anterior structure of the eye can be mapped in three dimensions by means of ultrasound biomicroscopy. The axial position of the anterior chamber angle, the iris and the ciliary sulcus can be unequivocally determined, and hence the location of the LHP for these placements. The position of the LHP for capsular bag placement can be related to the axial position of the anatomy proximal to the capsular bag equator, e.g. the equator itself, the zonula and/or the ciliary body.

With reference to:
18) Bell J. Interferometry reveals eye's microstructure. Opto & Laser Europe, Issue 12, August 1994, the location of the LHP can be directly determined by means of both optical coherence tomography and optical coherence microscopy.

The location of the LHP can also be determined by means of Scheimpflug photography in that Scheimpflug cameras are generally available nowadays.

Following schemes in a general text book on optics, namely:
19) O'Shea D C. Elements of modern optical design. New York, Wiley-Interscience, 1985, ray-tracing calculations for the paraxial ray, a meridional ray or any other ray, can be made. The paraxial ray-trace is tantamount to the application of thick lens theory, also known as Gaussian optics. The meridional ray-trace employs exact geometrical optics. The meridional and the paraxial ray-traces are equivalent for rays close to the optical axis.

A more sophisticated method to obtain best focus is by so called modulation transfer function (MTF) calculations. The performance of an optical system is best described by its optical transfer function (OTF). OTF has a real part, MTF, and an imaginary part, PTF (phase transfer function). Usually, one is only concerned about the MTF for which a theoretical upper limit, the diffraction limit, exists.

It is important that an optical system transfers spatial frequencies with a minimum of distortion.

The modulation, commonly called the MTF, is normalized to be 1 at zero spatial frequency (very large objects). The limiting MTF curve monotonically approaches 0 at the Rayleigh limit, the highest spatial frequency (finest detail) that can be transmitted by the optical system. The MTF curves of real systems obviously fall below the limiting curve.

The best focus, defined as the position at which MTF is maximal, of a system depends to some extent on the spatial frequency being focused at. A spatial frequency of 100 cycles per millimetre corresponds approximately to a level of fineness associated with visual acuity 20/20 (American terminology); 1.0 (European terminology); which is the line on the Snellen chart eye doctors and opticians consider as "full" vision.

For an optical system, one can calculate the maximum MTF for any given spatial frequency, wherein 100 cycles per millimetre would be a logical choice. The calculation is either "geometrical" or "diffractive". The latter is more precise and takes the wave nature of light into account. The calculation can also take the Stiles-Crawford effect into account. The retinal receptors are more sensitive for light perpendicular to the retinal surface. This directional preference is the Stiles-Crawford effect.

The "best" focus obtained by MTF calculations—or meridional ray-tracing—typically lies in front of the paraxial focus. At present, the measurement precision for IOL power calculation does not warrant more sophistication than the paraxial ray-trace (Gaussian optics).

The great advantage of the method according to the invention in comparison to methods known so far, is that it enables the calculation of IOL implant power on preoperatively measurable parameters, that it relates the IOL placement to the anatomy of the eye and that it is independent of intraocular lens models, provided that IOL manufacturers divulge the necessary design information.

The basic idea of the invention is to calculate where along the eye's optical axis the implanted IOL must be positioned in order to satisfy the optical condition to focus on the retina, given the pre-clinical eye measurements and the desired postoperative refraction.

To postoperatively measure ACD serves as an independent corroboration of the correctness of the calculation. If there are no measurement errors, the calculated ACD (anterior cornea to anterior IOL) and the measured ACD (geometrical) should coincide.

With a manufacturer's knowledge of the exact design of an IOL model, there is a simple geometric relationship between the position of the LHP and ACD. The offset between the LHP and the anterior vertex of the IOL depends on the design of the lens and its dioptric power, hence the relationship between LHP and ACD.

For any new IOL model, the dioptric power to render the eye emmetropic or with any desired refractive performance can be calculated, without recourse to ACD constants, A-constants, or any other type of constants, which is the practice today.

What is claimed is:

1. A method of preoperatively selecting the power of an intraocular lens to be implanted into an eye having a lens haptic plane, a corneal power, an axial length and ocular fluids, to postoperatively render the eye emmetropic or ametropic with a desired postoperative refraction, comprising the steps of a) determining the corneal power of the eye;

b) determining the axial length of the eye, c) choosing the desired postoperative refraction rendering the eye emmetropic or ametropic, d) determining the location of the lens haptic plane of the eye, e) selecting an intraocular lens for calculation, said lens having a known power and geometry, including an offset between the lens haptic plane and an anterior vertex of said lens as if it was in its implanted state, f) calculating from the parameters given by a), b), c), d) and e), and refractive indices of the ocular fluids, whether or not, postoperatively, focus will fall on the retina of the eye and if, from the calculation, it is determined that the focus will not fall on the retina of the eye, (i) selecting another intraocular lens with a different power and/or geometry for calculation, and (ii) repeating the calculation, steps (i) and (ii) being repeated until focusing on the retina is calculated, and g) selecting for implantation, a lens of the nearest power available for which focusing on the retina is calculated in step f).

2. The method as claimed in claim 1, wherein determining the location of the lens haptic plane comprises measuring a distance from an anterior cornea to an anterior cataract in the eye, measuring a thickness of the cataract, and adding said measured thickness, multiplied by a clinically determined constant, to said measured distance.

3. The method as claimed in claim 2, wherein said constant is between 0 and 0.25.

4. The method as claimed in claim 3, wherein said constant is between 0.15 and 0.2.

5. The method as claimed in claim 2, wherein said distance and said thickness are measured by ultrasound biometry.

6. The method as claimed in claim 1, wherein determining the location of the lens haptic plane comprises measuring a distance from an anterior cornea to an anterior cataract in the eye, measuring a thickness of the cataract, and multiplying said measured distance added to said measured thickness by a clinically determined constant.

7. The method as claimed in claim 6, wherein said constant is between 0.3 and 0.7.

8. The method as claimed in claim 7, wherein said constant is around 0.5.

9. The method as claimed in claim 6, wherein said distance and said thickness are measured by ultrasound biometry.

10. The method as claimed in claim 1, wherein the location of the lens haptic plane is directly determined.

11. The method as claimed in claim 10, wherein the location of the lens haptic plane is determined by means of ultrasound biomicroscopy.

12. The method as claimed in claim 10, wherein the location of the lens haptic plane is determined by means of optical coherence tomography.

13. The method as claimed in claim 10, wherein the location of the lens haptic plane is determined by means of optical coherence microscopy.

14. The method as claimed in claim 10, wherein the location of the lens haptic plane is determined by means of Scheimpflug photography.

15. The method as claimed in claim 1, wherein the calculations in step f) are conducted by optical-tracing, by thin lens calculations or by thick lens calculations.

16. The method as claimed in claim 1, wherein the calculations in step f) are conducted by computation of a maximum obtainable modulation of an optical transfer function of a spatial frequency.

17. The method as claimed in claim 16, wherein the spatial frequency is 100 cycles per millimetre.

* * * * *